(12) United States Patent
Wenner

(10) Patent No.: US 7,112,752 B1
(45) Date of Patent: *Sep. 26, 2006

(54) SYSTEM AND METHOD TO DELAY ACTIVATION OF A POWERED DEVICE

(76) Inventor: Justin B. Wenner, 12227 Everglade St., Los Angeles, CA (US) 90066

( * ) Notice: Subject to any disclaimer, the term of this patent is extended or adjusted under 35 U.S.C. 154(b) by 0 days.

This patent is subject to a terminal disclaimer.

(21) Appl. No.: 10/816,096

(22) Filed: Apr. 1, 2004

Related U.S. Application Data

(63) Continuation-in-part of application No. 09/955,610, filed on Sep. 19, 2001, now Pat. No. 6,635,834, and a continuation-in-part of application No. 10/664,778, filed on Sep. 17, 2003, now Pat. No. 6,846,994.

(51) Int. Cl.
*H01H 29/00* (2006.01)
(52) U.S. Cl. ............................ 200/61.04; 200/61.45 M; 600/343
(58) Field of Classification Search ............. 200/61.04, 200/61.08, 52 R; 600/343, 350, 380
See application file for complete search history.

(56) References Cited

U.S. PATENT DOCUMENTS

| | | | | | |
|---|---|---|---|---|---|
| 3,415,189 | A | * | 12/1968 | Trevorrow | 102/202.6 |
| 3,868,485 | A | * | 2/1975 | Sykes et al. | 200/61.2 |
| 3,997,886 | A | * | 12/1976 | Lerner | 137/88 |
| 4,313,042 | A | * | 1/1982 | Ehrhart | 200/61.04 |
| 5,846,744 | A | | 12/1998 | Athey et al. | |
| 5,848,744 | A | * | 12/1998 | Dischner et al. | 224/404 |
| 6,330,465 | B1 | * | 12/2001 | Huyberechts et al. | 600/343 |

* cited by examiner

*Primary Examiner*—K. Lee
*Assistant Examiner*—Richard K. Lee

(57) ABSTRACT

A system and method for delaying the activation of a powered device, such as a battery powered device. The activation of the device is triggered by contact with a particular environmental characteristic encountered by the device. For example, the system can be configured to activate upon contact with a particular pH value. Upon contact with the particular environmental characteristic, the restraining component (such as a magnetic field or a separating member) that prevents activation of the device is moved, modified, or caused to yield such that the device is activated.

27 Claims, 5 Drawing Sheets

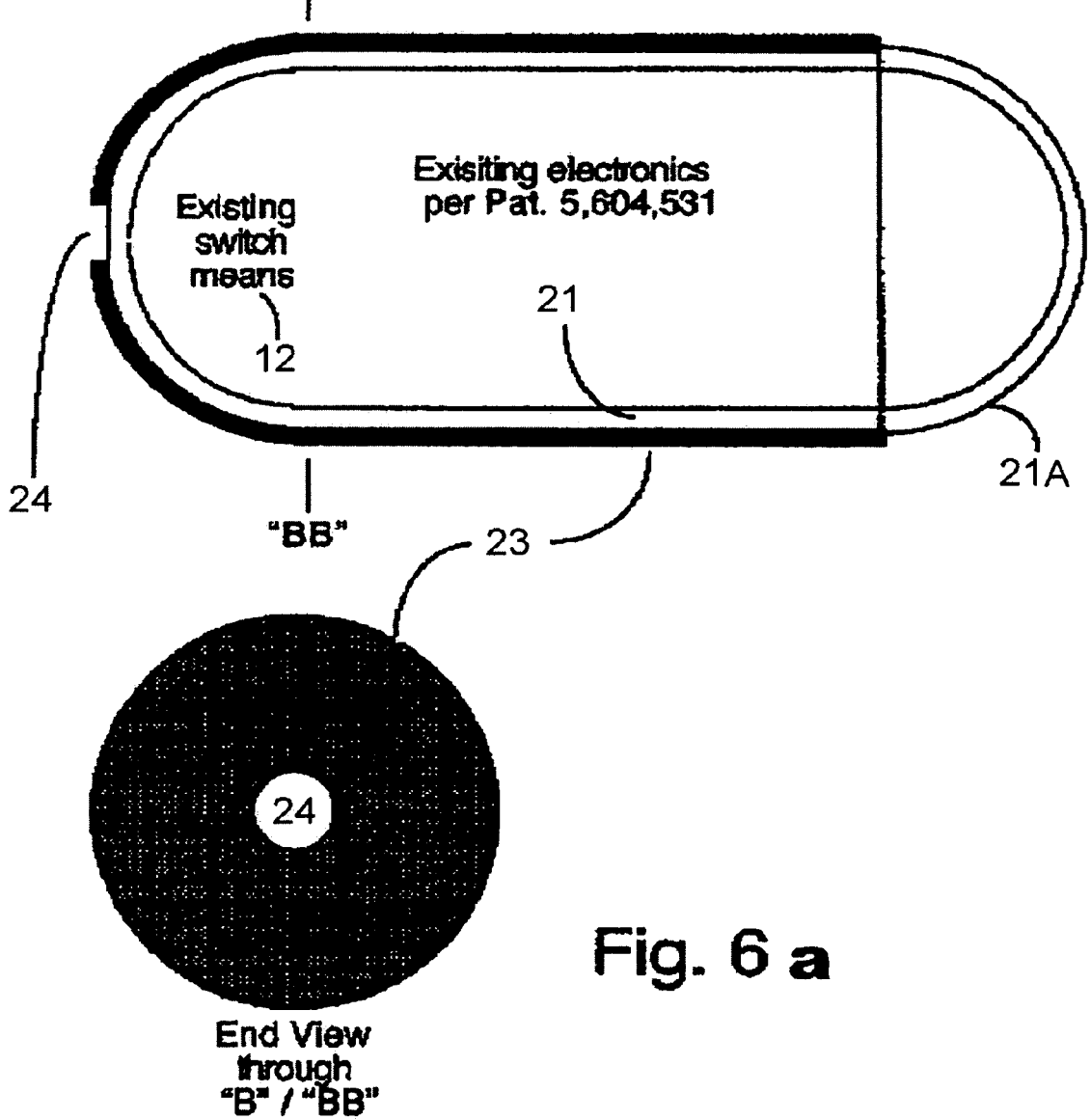

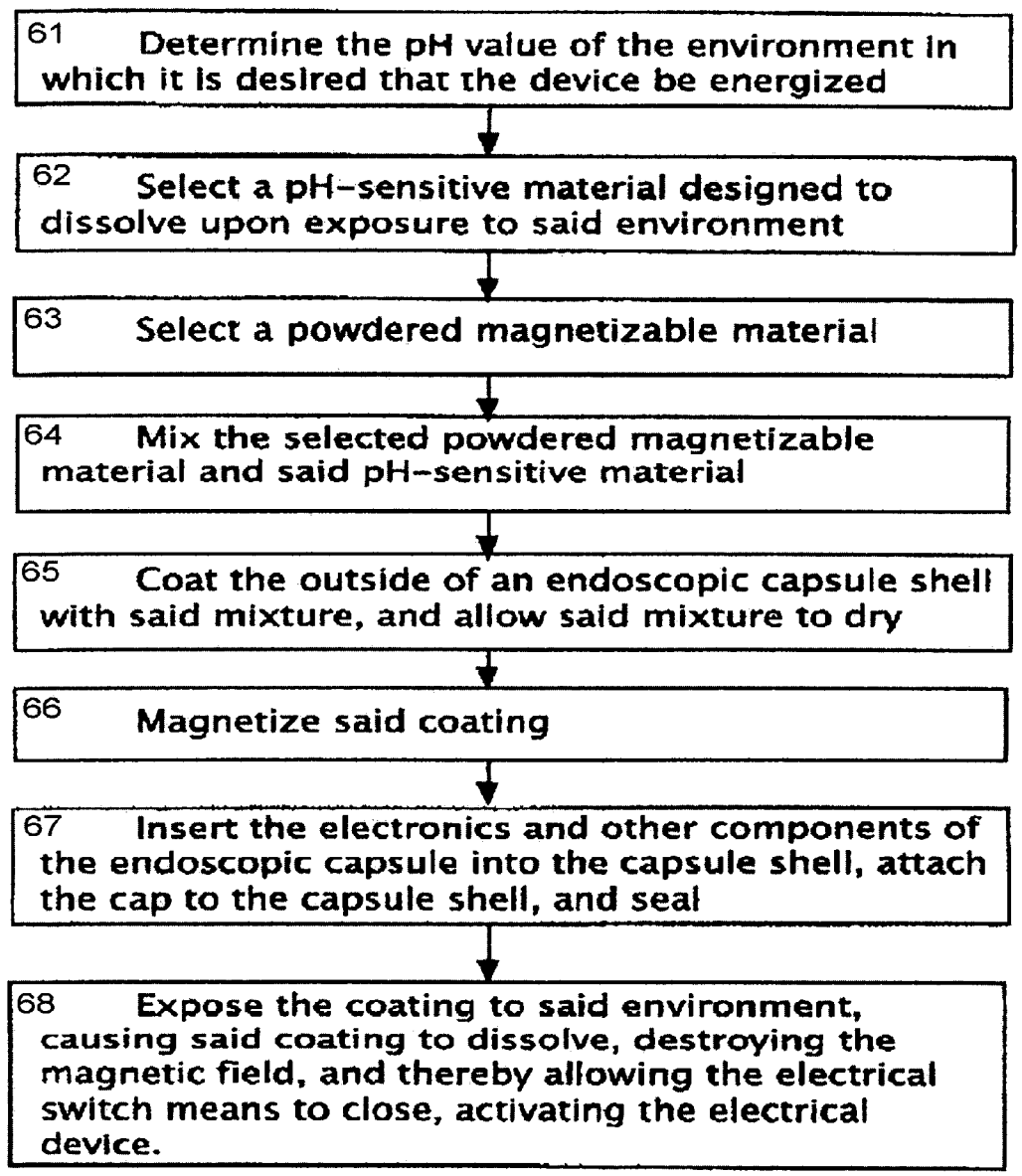

SYSTEM AND METHOD TO DELAY ACTIVATION OF A POWERED DEVICE

RELATED APPLICATIONS

The present continuation-in-part application claims priority from the utility patent application titled "SYSTEM AND METHOD TO DELAY CLOSURE OF A NORMALLY CLOSED ELECTRICAL CIRCUIT" (application Ser. No. 09/955,160) that was filed on Sep. 19, 2001 now U.S. Pat. No. 6,635,834, and the continuation-in-part application titled "SYSTEM AND METHOD TO DELAY CLOSURE OF A NORMALLY CLOSED ELECTRICAL CIRCUIT (application Ser. No. 10/664,778) filed on Sep. 17, 2003 now U.S. Pat. No. 6,846,994, the contents of which are hereby incorporated by reference in their entirety.

BACKGROUND OF THE INVENTION

The invention generally relates to delaying activation of a powered device until its activation is desired. In some embodiments of the invention, an endoscopic camera incorporates a system for delaying activation of the camera in a human body until it is properly situated for use. Different embodiments can involve a wide variety of different devices and different operating environments.

Colon cancer is the second leading cause of death in humans. It is curable if it is detected early. The current method of choice for early detection of colon cancer is a colonoscopy. Unfortunately, for many, colonoscopy is an expensive and uncomfortable procedure. Also, there is a risk that the colon may be punctured during the procedure. Consequently, many people opt to avoid or postpone the procedure. As a result, thousands of people die every year because they do not get a colonoscopy.

A less intrusive and cheaper method for early detection of cancer has been developed. It is described in U.S. Pat. No. 5,604,531 to Iddan, et al. that issued on Feb. 18, 1997. In this method, a small endoscopic capsule is swallowed. The capsule contains, inter alia, a means for illumination, a video camera, a lens arrangement and a transmitter. The capsule travels through the body, taking pictures along the alimentary canal and transmitting them to a receiver attached to a belt worn by the patient. Patients are permitted to move around normally during the approximately eight hour procedure. Since the device must be small enough to be swallowed, the size of its power source, a battery, and the amount of power it can provide are severely limited. Further, the capsule must be turned on before it is swallowed. Therefore, the principal disadvantage of this device is that the power source is depleted before it completes an investigation of the small intestine and colon. Consequently, the device is unable to investigate for cancer and other abnormalities in these parts of the body. The present invention solves this problem by delaying activation of devices, such as this capsule, until the capsule enters a particular part of the body.

There are several patents covering methods used to delay activation of electrically powered devices until they are needed. U.S. Pat. No. 5,057,824 to Stokes that issued on Jul. 30, 1990, uses a normally closed switch held open by a removable spacer. It is designed to be used in security systems to conserve battery power until the device is ready for use. Upon manual removal of the spacer the switch closes and power is supplied. The principle disadvantage of this method is that it must be activated manually, and thus cannot be activated while in an environment that is not directly accessible, such as the human alimentary canal. If the removable spacer method were used to delay activation of the endoscopic capsule in U.S. Pat. No. 5,604,531, it would need to be activated prior to being swallowed; accordingly, the device would still run out of power prior to completing an investigation of the small intestine and colon.

U.S. Pat. No. 4,278,077 to Mizumoto that issued on Jul. 14, 1981 uses an induction system to energize an electromagnetic field in a coil around a permanent magnet located in the device. This method energizes the device when it is needed. The principal disadvantage of this device is that it requires the patient to remain in a stationary position during the entire 8 hour process. Furthermore, this method cannot be used to energize the endoscopic capsule described in U.S. Pat. No. 5,604,531 to Iddan, et al. due to size constraints.

SUMMARY OF THE INVENTION

The present invention is a system and method to delay activation of a powered device (collectively the "system"). The delayed activation of a powered device can be achieved by the delayed closure of an electrical circuit of a battery-powered electrical device. The system can be embodied in a swallowable endoscopic capsule that is intended to operate remotely in an environment in which the pH value changes from one value to another. More specifically, a pH-sensitive material, used either alone or in conjunction with a Hall effect transistor and a magnet, or in conjunction with a Hall effect transistor and a mixture of the pH-sensitive material and a magnetizable material, holds the electrical circuit open, or the Hall effect transistor in a nonconducting mode, until the device is exposed to an environment having a specified pH value. Exposure of the pH sensitive material to an environment having that specified pH value causes the pH-sensitive material to dissolve. The dissolving of the material causes the circuit to close, or the Hall effect transistor to be in a conducting mode, energizing the device. Different embodiments of the system can trigger the delayed activation of a device based on different characteristics of the desired operating environment.

Accordingly, several objects and advantages of the invention are to provide a means to delay activation of a powered device by holding it in a deactivated condition until ready for use.

An object of the present invention can be to provide a means by which an electrical device can be self-activated at a specific point within an environment that is difficult to access, such as the human alimentary canal.

Another object of the present invention can be to use the pH value of an environment to dissolve a pH-sensitive material separating electrical contacts to activate a battery powered electrical device.

Still another object of the present invention can be to use the pH value of an environment to dissolve a pH-sensitive material holding a magnet against a battery-powered electrical device, causing the magnet and battery-powered electrical device to separate, causing a Hall effect transistor to conduct, to activate a battery-powered electrical device.

Yet another object of the present invention can be to use the pH value of an environment to dissolve a magnetizable coating applied to the outside of a battery-powered electrical device, said coating consisting of a mixture of a pH-sensitive material and a magnetizable material, to activate a battery powered electrical device.

Further objects and advantages of the invention are apparent to those skilled in the art from review of the process flow chart, drawings and description of a preferred embodiment and alternate embodiments.

BRIEF DESCRIPTION OF THE DRAWINGS

The system can be understood more fully from the following description taken in conjunction with the drawings in which:

FIG. 6 is a schematic view illustrating an alternative example of an embodiment of the system that includes an endoscopic camera unit.

FIG. 6a is an end view of the endoscopic camera unit shown in FIG. 6.

FIG. 7 is a process flow chart illustrating an example of a process for delaying activation of a device.

DETAILED DESCRIPTION

One category of embodiments of the system is primarily intended for use with a swallowable endoscopic capsule, as described in U.S. Pat. No. 5,604,531 to Iddan, et al. that issued on Feb. 18, 1997. The endoscopic capsule described in that patent is designed to take pictures of the human alimentary canal. In this prior art, the endoscopic capsule travels through the alimentary canal from the mouth to the stomach, small intestine and colon. Battery capacity is necessarily limited due to size constraints. Its batteries must be activated before it is swallowed, and the device tends to run out of battery power before reaching the colon.

The system delays activation of the electronic components of the endoscopic capsule device until just prior to reaching the small intestine so that it has enough remaining battery power to operate while traveling through the small intestine and the colon.

Many embodiments of the system described below use a pH-sensitive material, used either alone (as an insulating element) or in conjunction with a Hall effect transistor and a magnet or magnetizable material. The pH-sensitive material can act to hold an electrical circuit open until the device is exposed to an environment having a specified pH value. Exposure of the pH sensitive material to an environment having that specified pH value causes the pH-sensitive material to dissolve. The dissolving of the material causes the circuit to close, or the Hall effect transistor to be in a conducting mode, powering the device.

All embodiments described below use a pH-sensitive material designed to dissolve when exposed to an environment having a specified pH value. The preferred material is made by Colorcon Company of West Point, Pa. 19486, described in U.S. Pat, No. 5,811,121 to Wu, et al. that issued on Sep. 22, 1998. That material is sold under the trademark name of SURETERIC.

Figures 2, 3:
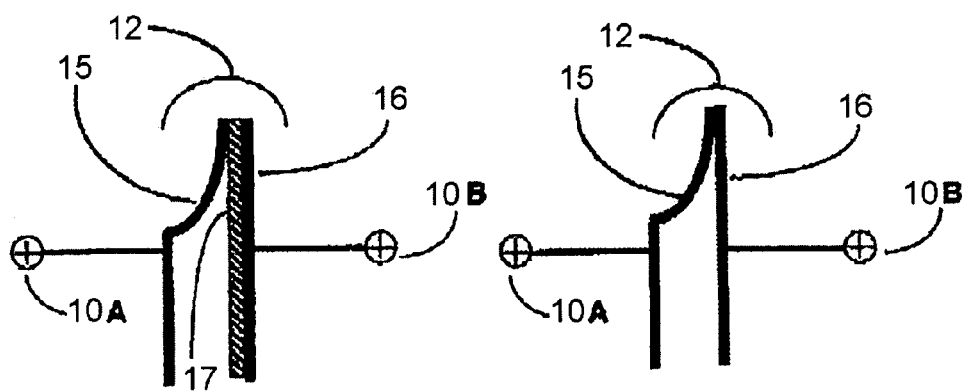
FIG. 2 shows a diagram illustrating an example of a normally closed switch held open by the pH-sensitive material separating the contacts.
FIG. 3 shows a diagram illustrating an example of a normally closed switch after the pH-sensitive material has dissolved.

FIG. 2 shows the preferred embodiment having a normally closed switch connected in series between the battery and electrical circuitry of a swallowable endoscopic capsule and held open by a pH-sensitive insulating element 17. The normally closed switch 12 has a movable contact 15 and a stationary contact 16. Pursuant to the preferred embodiment of the present invention, the stationary contact 16 is coated with a pH-sensitive element 17 designed to dissolve when exposed to an environment having a specified pH value. The material 17 holds the movable contact 15 separate from the stationary contact 16, keeping the battery 11 (or some other power source) and the powered device (such as a battery-powered device) 13 inactive. Color may be added to the material 17 to allow for easy identification of differing pH values. The movable contact 15 and stationary contact 16 may be made of various materials, including, but not limited to, brass, copper and phosphor bronze.

Figure 1:
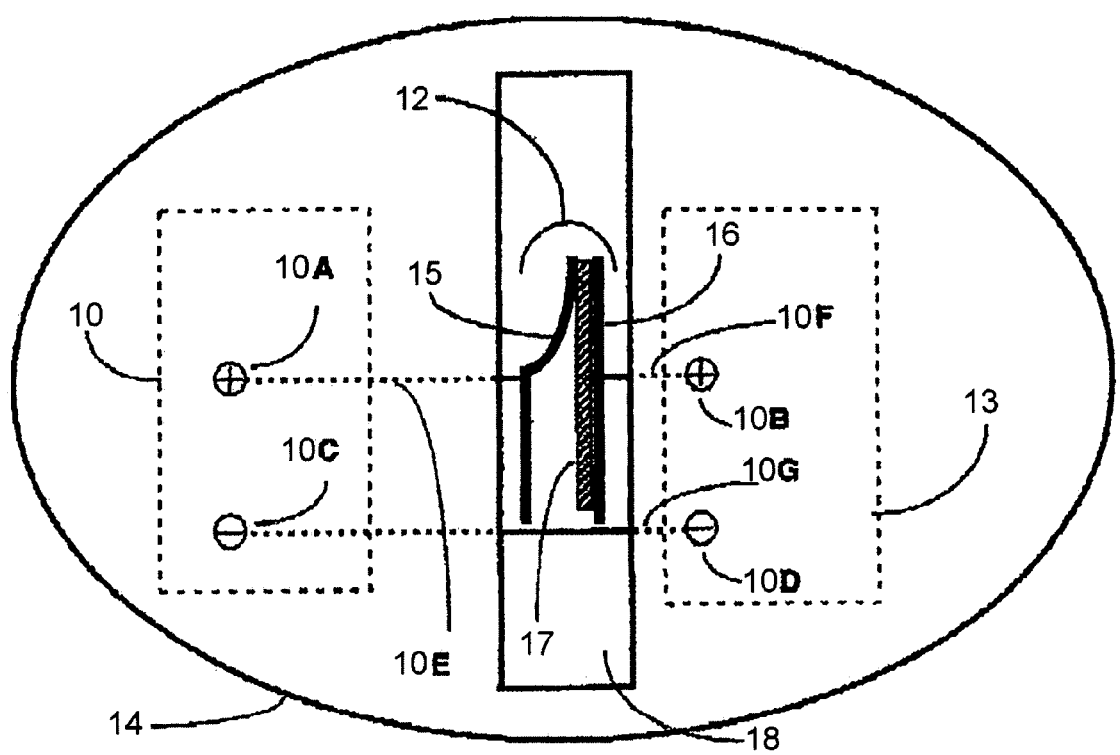
FIG. 1 shows a diagram illustrating an example of a normally closed switch held open by a pH-sensitive material and connected in series between the battery and the electrical circuitry of a swallowable endoscopic capsule.

As shown in FIG. 1, the protective covering 14 of the endoscopic capsule contains an opening 18, allowing the material 17 coated on the stationary contact 16 to be exposed directly to the various environments of the alimentary canal as the capsule travels from the mouth through the stomach, small intestine and colon. Each region through which the capsule travels, during at least part of its journey, has an ever-increasing pH value, starting with a value of pH 1–2 in the stomach and finally reaching a value above pH 7 in the colon. The material 17 that holds the switch 12 open will dissolve upon reaching a region in which the pH value is greater than that of the material 17. For example, if the stationary contact 16 is coated with a material with a pH of 4, it will dissolve after leaving the stomach and before reaching the colon. Once the material 17 is dissolved, the switch 12 will close, causing the battery 11 to provide power to electrically powered device 3.

FIG. 1 shows a battery 11 inside protective cover 14, which contains opening 18. Opening 18 exposes to the outside environment only that section of the capsule containing the switch. It is unnecessary, and may be undesirable, to expose the other capsule components. Positive electrode 11A of battery 11 is connected to movable contact 15 of a normally closed switch 12 by wire 11E, and stationary contact 16 of switch 12 is connected to the positive lead 11B of electrically powered device 13 by wire 1F. Negative electrode 11C of battery 11 is connected to the negative lead 11D of 13 by wire 11G.

As shown in FIG. 2, switch 12, which is normally biased toward its closed position, has movable contact 15 which is held apart from stationary contact 16 by insulating material 17 that is designed to dissolve at a specified pH value. The material 17 prevents electrical current from flowing from positive electrode 11A to positive lead 11B.

FIG. 3 shows a normally closed switch 12 after the material 17, shown in FIG. 2, dissolves. Accordingly, FIG. 3 shows a normally closed switch 12 with movable contact 15 closed against stationary contact 16, allowing current to flow from positive electrode 11A to positive lead 11B.

Figure 4:
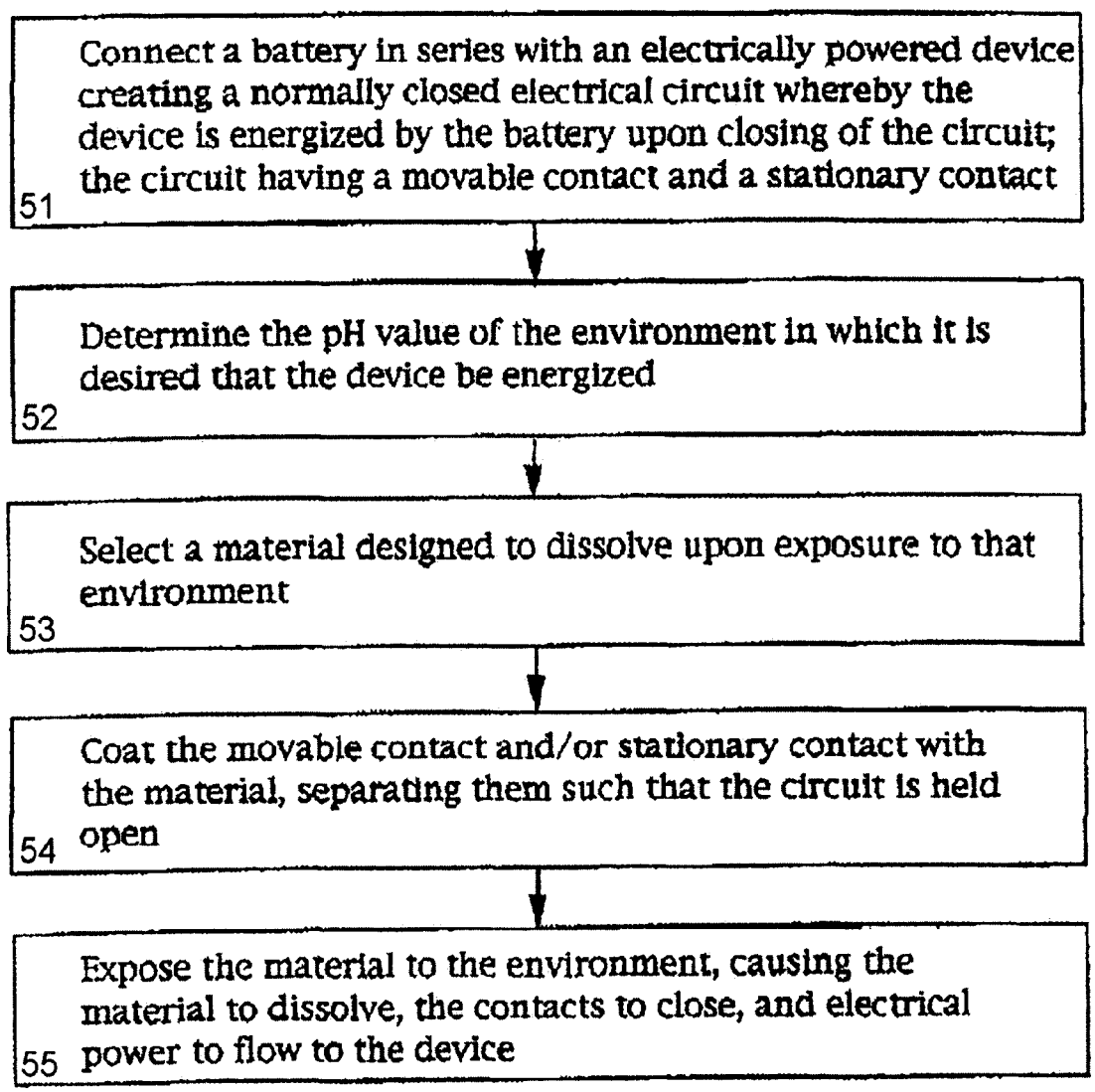
FIG. 4 is a process flow chart illustrating an example of a process for delaying activation of a device.

FIG. 4 is a process flow chart for the preferred embodiment of the present invention. At step 51, a battery is connected in series with an electrically powered device, creating a normally closed electrical circuit whereby the device is energized by the battery upon closing of the circuit. The circuit has a movable contact and stationary contact. At step 52, the pH value of the environment in which it is desired that the device be energized is determined. At step 53, a material designed to dissolve upon exposure to that environment is selected. At step 54, either the movable contact and/or stationary contact is coated with the material, separating them such that the circuit is held open. Finally, at step 55, the material is exposed to the desired environment, causing the material to dissolve, the contacts to close, and electrical power to flow to the device.

As an alternative embodiment, the pH-sensitive insulating material is applied directly to the positive and/or negative ends of at least one battery within the circuit. The material holds the circuit open until the material dissolves. When the material dissolves, a movable contact holding the battery in place closes against the battery, allowing current to flow.

In two alternative embodiments, the switch means utilized to complete the circuit and power the capsule's components is a Hall effect transistor or similar circuitry such as a reed switch. The Hall effect transistor is operable to open the capsule's electrical circuit when it is in the presence of a magnetic field, and to close the capsule's electrical circuit (thus powering the capsule's camera and transmitter components) when the magnetic field is absent. A reed switch consists of two magnetic contacts in a tube. When a magnet is close to a reed switch, the two contacts become magnetized and repel each other, blocking electrical current. When the magnet is moved away from the reed switch the contacts demagnetize and move to their original, closed position.

Figure 5:
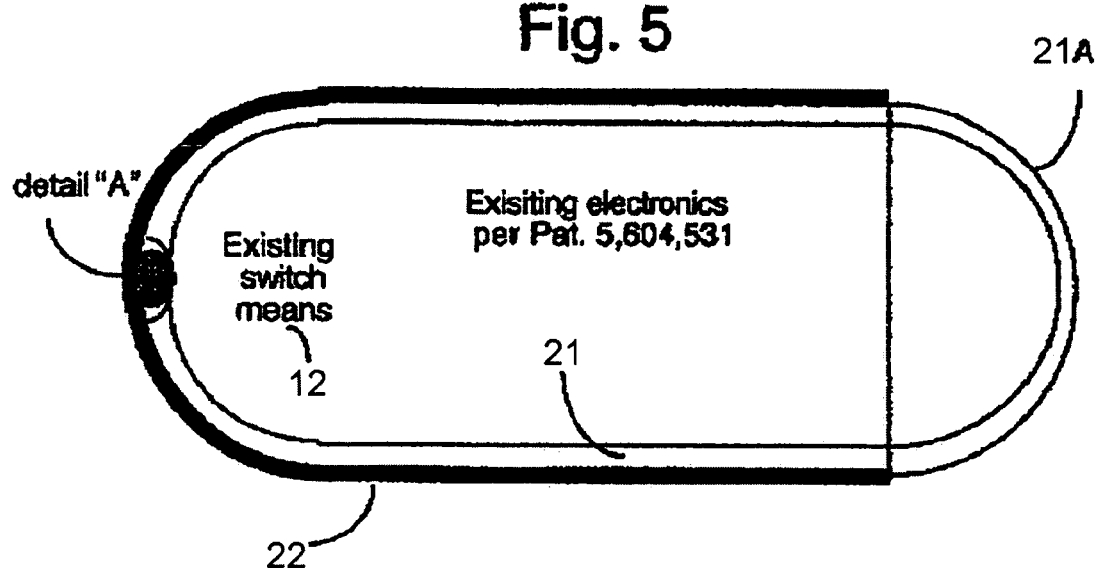
FIG. 5 is a schematic view illustrating an example of an embodiment of the system that includes an endoscopic camera unit.
Figure 5A:
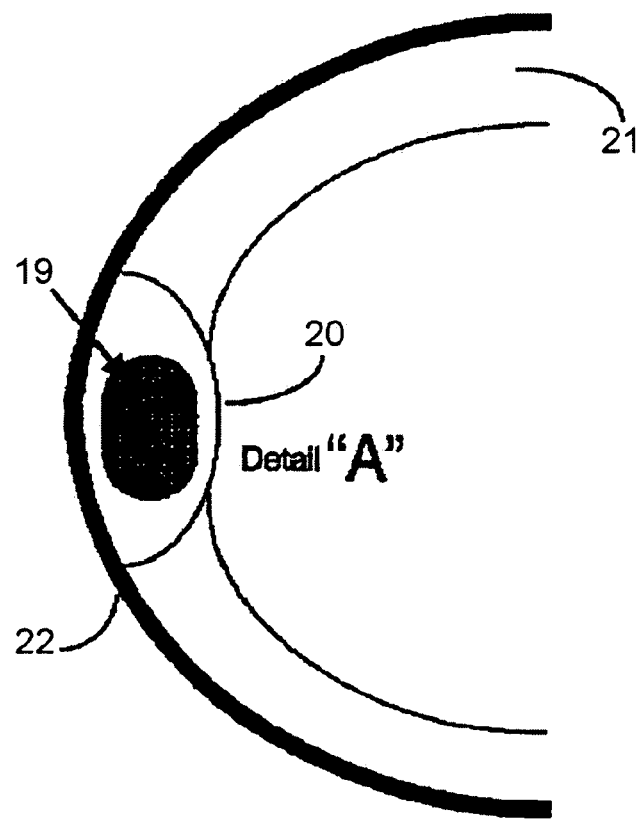
FIG. 5a is an enlarged detail view of the endoscopic camera unit shown in FIG. 5.

In an alternative embodiment schematically shown in FIGS. 5 and 5a, small magnet 19 is held in dimple 20 in the end of the endoscopic capsule. The capsule is then coated with the pH-sensitive material, holding the magnet in place against the capsule. The magnet's magnetic field holds a Hall effect transistor inside the capsule a nonconducting mode. Exposure of the material to an environment having a specified pH value causes the pH-sensitive material to dissolve, causing the magnet and capsule to separate, causing said Hall effect transistor to conduct, energizing said capsule.

In another alternative embodiment schematically shown in FIGS. 6 and 6a, the pH-sensitive material is mixed with a magnetizable material, such as an iron powder, creating a magnetizable coating. The coating is applied to the outside of the swallowable endoscopic capsule. When the coating is magnetized, the resulting magnetic field maintained between opposite poles at central opening 24 and distal opening holds a Hall effect transistor in a non-conducting mode. Exposure of the coating to an environment having a specified pH value causes the pH-sensitive material to dissolve, destroying the magnetic field. The destruction of the magnetic field causes the Hall effect transistor to conduct, thus activating the camera and transmitter circuitry in the swallowable endoscopic capsule.

The embodiment schematically depicted in FIG. 5 utilizes a magnetic field to hold the electrical switch means in a non-conducting mode until the magnetic field is destroyed. FIG. 5 shows some, but not all, of the components of an endoscopic capsule: a shell 21, shell cap 21A, and an electrical switch means 12. In this embodiment, magnet 19 is placed in a dimple 20 at the end of shell 21. A coating 22 is applied to both the magnet 19 and the outside of shell 21, such that when coating 22 dries and hardens, magnet 19 is held in place in dimple 10 at the end of shell 21. The preferred magnet is a rare earth magnet. The preferred coating is the pH-sensitive material described above. Alternatively, magnet 19 can be coated in place against the end of shell 21 without the need for a dimple. The magnet 19 will hold an electrical switch means 12, which is part of the electrical circuit of the endoscopic capsule, in a non-conducting mode. The preferred switch means is either a Hall effect transistor or a normally closed switch means. Exposure of the coating to an environment having a specified pH value causes the coating to dissolve, and causes the magnet to separate from the shell. This separation removes the capsule from the magnetic field, allowing the Hall effect transistor to conduct, thus activating the electronics of the endoscopic capsule where needed.

FIG. 6 shows another alternative embodiment. Similar to the second alternative embodiment described above, this embodiment also utilizes a magnetic field to hold the electrical switch means in a non-conducting mode until the magnetic field is destroyed. The main difference is that, rather than using a discrete magnet, this embodiment employs a magnetizable coating 23 on the outside of shell 21 of the endoscopic capsule. The preferred coating 23 is a mixture of the pH-sensitive material, described above, and a powdered magnetizable material. The preferred magnetizable material is powdered iron, powdered rare earth or powdered Alnico. Coating 23 is magnetizable.

Coating 23 is applied to the outside of the shell 21. The area of the coating at the end of the shell 21 has an opening 24 to focus the magnetic field. It is preferable that the shell 21 be coated prior to placing any electronics inside the shell. After coating 23 is applied to the shell 21, the coating 23 is magnetized. When magnetized, said coating 23 will hold an electrical switch means, which is part of the electrical circuit of the swallowable endoscopic capsule, in a non-conducting mode. The preferred switch means is either a Hall effect transistor or a normally closed switch means. Exposure of the coating 23 to an environment having a specified pH value causes the material to dissolve, which allows the magnetic field formed by the coating 23 to be destroyed, allowing the Hall effect transistor to conduct, or the said switch means to close, thus activating the electronics of the endoscopic capsule where needed. As an example, the electronics of the endoscopic capsule can be activated in the stomach, intestine, colon, or other environment along the alimentary canal, based on the predetermined pH level at which the coating is set to dissolve.

FIG. 7 is a process flow chart describing the third alternative embodiment for the present invention. At step 61, the pH value of the environment in which it is desired that the electronic device be activated is determined. At step 62, a material designed to dissolve upon exposure to said environment is selected. At step 63, a powdered magnetizable material is selected. At step 64, said powdered magnetizable material and said pH-sensitive material are mixed. At step 65, the mixture is applied to the outside of an endoscopic capsule shell, and is allowed to dry, forming a coating. At step 66, said coating is magnetized. At step 67, the electronics and other components of the endoscopic capsule are inserted into the shell, and the shell cap is attached to the shell, and the capsule is sealed closed. At step 68, the coated endoscopic capsule is exposed to an environment having the pH value determined in step 1 above, causing the coating to dissolve, destroying the magnetic field, and thereby allowing electrical power to flow, activating the electrical device.

From the above, it should be understood that the embodiments described, in regard to the drawings, are merely exemplary and that a person skilled in the art may make variations and modifications to the shown embodiments without departing from the spirit and scope of the invention. All such variations and modifications are intended to be included within the scope of the invention as defined by the appended claims. This information is meant to be illustrative and not limiting.

The concepts identified and described above can be implemented in a wide variety of different embodiments. For example, a wide variety of different devices can be incorporated into the system. Similarly, a wide variety of different environmental characteristics can be used to trigger the activation of the device. A wide variety of different restraining components, such as magnetic fields and separation members can be used to delay activation of the various devices.

The invention claimed is:

1. A system for delaying activation of a powered device intended to operate remotely in an environment in which an environmental attribute changes from a first value to a second value, comprising:
   a housing;
   a restraining component proximally associated with said housing, said restraining component being separable from said housing upon exposure to an environment having an environmental attribute less than or about equal to said second value;
   a normally closed electrical circuit disposed in said housing; said circuit having a power source connected with the powered device, whereby the powered device is powered upon the closing of said circuit;
   said circuit having a switch sensitive to the presence of said restraining component; said switch being configured to open said circuit in the presence of said restraining component and to close said circuit in the absence of said restraining component;
   whereby when said housing encounters an environment having said environmental attribute less than or about equal to said second value, said restraining component separates from said housing and said circuit closes, powering said powered device.

2. The system of claim 1, further comprising a surface exterior to said housing, a coating, and a magnetic field source, wherein said magnetic field source is fixed to said surface by said coating.

3. The system of claim 2, wherein said magnetic field source comprises a magnet fixed to said surface by said coating.

4. The system of claim 3, wherein said magnet is disposed in a dimple defined in said surface.

5. The system of claim 2, wherein said coating comprises a pH-sensitive material.

6. The system of claim 1, wherein said housing is a swallowable capsule.

7. The system of claim 1, wherein said powered device includes a sensor.

8. The system of claim 1, further comprising a magnetic field source and a magnetic field, wherein said restraining component is said magnetic field source, wherein said switch is configured to open said circuit in the presence of said magnetic field, and wherein said switch is configured to close said circuit in the absence of said magnetic field.

9. The system of claim 1, further comprising a dissolvable material, wherein said restraining component is said dissolvable material, and wherein said dissolvable material is configured to dissolve upon exposure to said environment having said environmental attribute less than or equal to said second value.

10. The system of claim 1, further comprising a circuit and a magnetic field holding a Hall effect device in a nonconducting mode, wherein said magnetic field is separated from said housing, wherein said Hall effect device is configured to transition to a conducting mode, thereby closing said circuit and powering the powered device.

11. The system of claim 1, further comprising a switch and a magnetic field, wherein said switch is biased closed, but opened when influenced by said magnetic field.

12. The system of claim 11, wherein said switch includes a Hall effect device, said magnetic field holding said Hall effect device in a nonconducting mode, so that when said magnetic field is separated from said housing, said Hall effect device transitions to a conducting mode, thereby closing the circuit and powering the powered device.

13. The system of claim 12, wherein said Hall effect device is a Hall effect transistor.

14. The system of claim 11, wherein the size of the powered device is smaller than a comparable powered device not capable of remote or delayed activation.

15. The system of claim 1, further comprising a coating, wherein said coating is dissolvable upon exposure to an environment having an environmental attribute less than or about equal to said second value.

16. The system of claim 1, wherein said environment having said environmental attribute less than or about equal to said second value is an internal area of a human body.

17. The system of claim 16, wherein the human being need not be stationary.

18. The system of claim 1, wherein said environment is an alimentary canal.

19. The system of claim 1, wherein said restraining component is configured to dissolve in a predefined location within the human body.

20. The system of claim 1, further comprising a coating and a magnetizable material, wherein said coating includes a magnetizable material.

21. The system of claim 20, wherein said magnetizable material includes an iron powder.

22. The system of claim 1, wherein said restraining component includes a movable contact and a stationary contact.

23. The system of claim 22, further comprising a conductive material, wherein at least one of said movable contact and said stationary contact is made of said conductive material.

24. The system of claim 1, wherein only said restraining component is exposed to said environment with said environmental attribute of said second value.

25. The system of claim 1, wherein said system is an endoscopic capsule.

26. The system of claim 1, wherein said restraining component is a rare earth magnet.

27. A system for delaying activation of a battery-powered electrical device, intended to operate remotely in an environment in which a pH value changes from a first value to a second value, comprising:
   a housing defining an interior space and having an exterior surface;
   a magnetic field source proximally associated with said housing, said magnetic field source being separable from said housing upon exposure to an environment having a pH value equal to said second value;
   a normally closed electrical circuit disposed in said housing;
   said circuit having a battery connected in series with an electrically powered device, whereby said electrically powered device is powered by said battery upon closing of said circuit;

said circuit having switch means sensitive to the presence of a magnetic field associated with said magnetic field source;

said switch means operable to open said circuit in the presence of said magnetic field and to close said circuit in the absence of said magnetic field;

whereby when said housing encounters an environment having a pH value equal to said second value, said magnetic field source separates from said housing and said circuit closes, powering said electrically powered device;

wherein said switch means comprises a reed switch biased closed, but opened when influenced by said magnetic field.

* * * * *